(12) United States Patent
Nicolo

(10) Patent No.: US 6,279,809 B1
(45) Date of Patent: Aug. 28, 2001

(54) CIRCULAR STAPLER FOR SIDE TO END, SIDE TO SIDE AND END TO SIDE ANASTOMOSIS

(76) Inventor: Enrico Nicolo, 1515 Timerlane, Clairton, PA (US) 15025

( * ) Notice: Subject to any disclaimer, the term of this patent is extended or adjusted under 35 U.S.C. 154(b) by 0 days.

(21) Appl. No.: 09/264,764

(22) Filed: Mar. 9, 1999

Related U.S. Application Data

(60) Provisional application No. 60/077,393, filed on Mar. 10, 1998.

(51) Int. Cl.[7] .................................................. A61B 17/068
(52) U.S. Cl. ...................... 227/176.1; 227/19; 227/179.1; 606/219
(58) Field of Search .............................. 227/176.1, 175.1, 227/179.1, 19; 606/139, 219

(56) References Cited

U.S. PATENT DOCUMENTS

| | | | | |
|---|---|---|---|---|
| 3,638,652 | * | 2/1972 | Kelley | 227/179.1 |
| 4,615,474 | * | 10/1986 | Strekopytov et al. | 227/19 |
| 4,817,847 | * | 4/1989 | Redtenbacher et al. | 227/19 |
| 5,104,025 | * | 4/1992 | Main et al. | 227/19 |
| 5,197,648 | * | 3/1993 | Gingold | 227/19 |
| 5,411,508 | * | 5/1995 | Bessler et al. | 227/19 |
| 5,441,507 | * | 8/1995 | Wilk | 606/139 |
| 5,868,760 | * | 2/1999 | McGuckin, Jr. | 227/179.1 |
| 6,050,472 | * | 4/2000 | Shibata | 227/179.1 |
| 6,119,913 | * | 9/2000 | Adams et al. | 227/176.1 |
| 6,126,058 | * | 10/2000 | Adams et al. | 227/179.1 |

FOREIGN PATENT DOCUMENTS

| | | | | |
|---|---|---|---|---|
| 615922 | * | 7/1978 | (SU) | 227/176 |
| 1012896 | * | 4/1983 | (SU) | 227/176 |

\* cited by examiner

*Primary Examiner*—Scott A. Smith
(74) *Attorney, Agent, or Firm*—Webb Ziesenheim Logsdon Orkin & Hanson, P.C.

(57) ABSTRACT

A circular stapler for side to end, side to side or end to side anastomosis includes an actuating head portion attached to an elongated tubular body with a handle on the opposed end of the body from the head. The head includes an anvil and associated stapling mechanism, wherein the anvil and the associated stapling mechanism are positioned perpendicular to a longitudinal axis of the head. The anvil is releasably attached to the head and may be attached to the head through an anvil applicator. The anvil may include an extendable stem.

13 Claims, 2 Drawing Sheets

CIRCULAR STAPLER FOR SIDE TO END, SIDE TO SIDE AND END TO SIDE ANASTOMOSIS

This application claims the benefit of U.S. Provisional Patent Application Ser. No. 60/077,393 filed Mar. 10, 1998 entitled "Circular Stapler for Side to End, Side to Side and End to Side Anastomosis"

BACKGROUND OF THE INVENTION

1. Field of the Invention

I, Enrico Nicolo, have invented a surgical tool which relates to anastomotic staplers, more particularly, to a circular stapler for side to end, side to side or end to end anastomosis.

2. Background Information

In the anastomosis of two segments of a resected bowel, a surgical circular end to end anastomosis stapler is often used. These surgical tools are conventionally called "EEA staplers", "EEA devices" or simply "EEA's". These devices are used to attach one longitudinal, generally cut, end of a bowel segment to another longitudinal, generally cut, end of a bowel segment. I have discovered that it may be beneficial to attach the side of one bowel segment to the end or to the side of another bowel segment in a bowel resection, or the like. This procedure would be very helpful, for example, in performing the second stage of a two-stage Hartman operation. However, there are currently no surgical tools to easily accomplish this type of attachment.

An object of my invention is to provide a surgical anastomosis stapler which allows for the side of the lower bowel segment to be attached to the end or to the side of another bowel segment to be attached thereto. A further object of my invention is to provide a surgical circular anastomotic stapler which is easy to manufacture and does not differ significantly in operation from existing surgical staplers.

SUMMARY OF THE INVENTION

The above objects are achieved by providing a surgical circular stapler according to my invention which allows for side to end, side to side or end to side anastomosis. The stapler of my invention includes an actuating head portion attached to an elongated tubular body with a handle on the opposed end of the body from the head. The head includes an anvil and associated stapling mechanism, wherein the anvil and the associated stapling mechanism are positioned generally perpendicular to the longitudinal axis of the head.

The handle may include a rotary control for actuating the anvil of the stapler and a trigger for firing of the staples in the stapling mechanism. The handle may further include a conventional safety lock which acts to prevent firing of the staples until the anvil is in the appropriate position.

The end of the head may be rounded to minimize potential trauma to the bowel or other hollow viscus. The widest dimension of the head should be generally equal to the diameter of the circular head of a conventional EEA stapler, which is generally less than about 35 mm. The head further includes right angle drives for both the stapling mechanism and for operation of the anvil.

The present invention additionally includes an anvil applicator for receipt and delivery of the anvil of a surgical stapler where the anvil is to be attached to the head of the stapler at the anastomosis site. The anvil applicator may include a receiving sleeve and a reciprocating plunger within the sleeve. Another aspect of the present invention provides a modified anvil with an extended stem. The extended stem may be a telescoping member. The extended stem allows the surgeon to attach the anvil to the head of the stapler at a more convenient location for better access and control. Both the anvil applicator and the modified anvil are not limited for use with the stapler of the present invention, but may be used with conventional staplers.

These and other advantages of my invention will be clarified in the description of the preferred embodiments taken together with the attached drawings wherein like reference numerals represent like elements throughout.

DESCRIPTION OF THE PREFERRED EMBODIMENTS

Figures 1, 2:
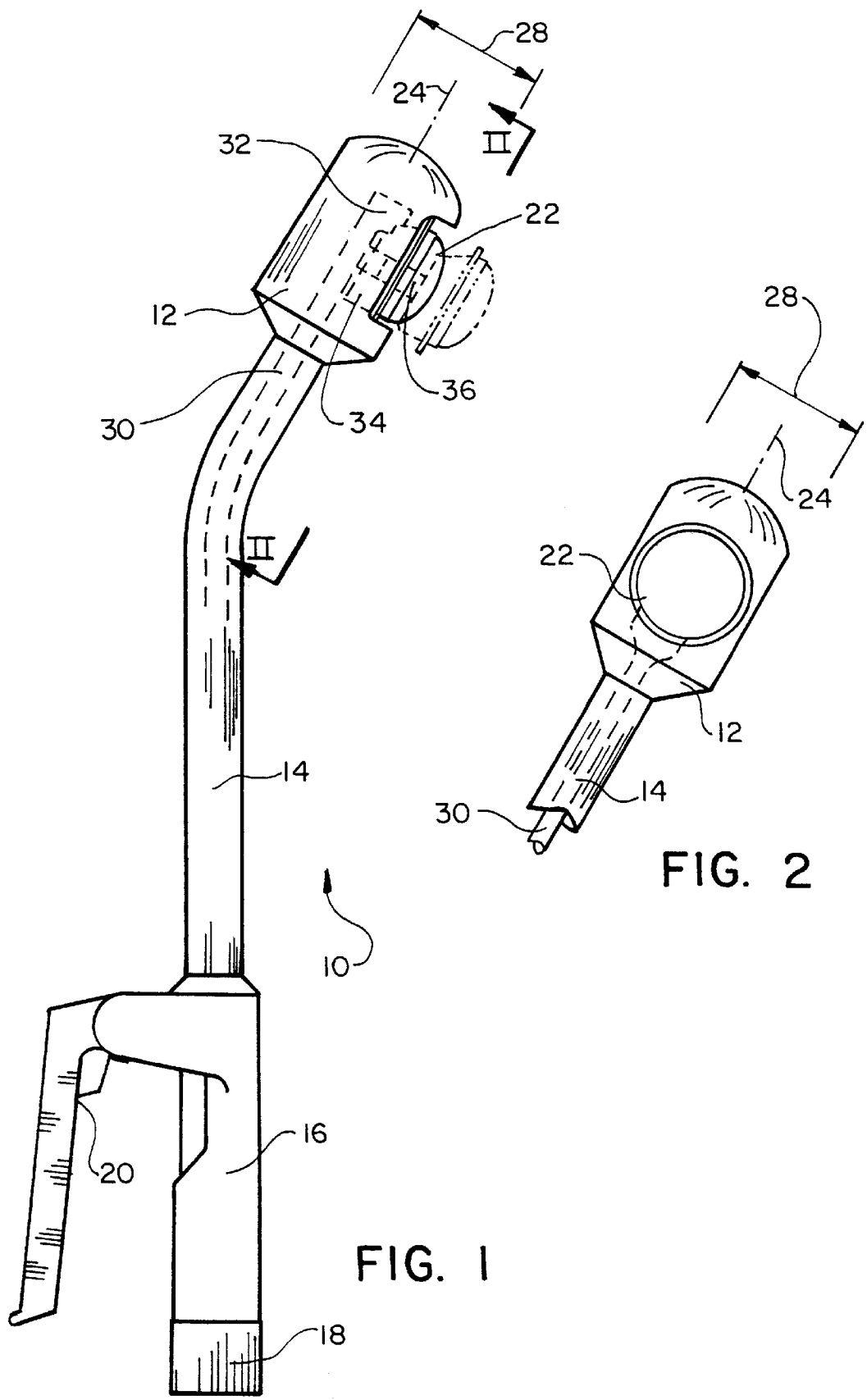
FIG. 1 is a perspective view of one embodiment of a circular stapler for side to end or side to side anastomosis according to my invention.
FIG. 2 is a front view of a head portion of the stapler illustrated in FIG. 1.

A surgical circular stapler 10 for side to end or side to side anastomosis according to my invention is illustrated in FIGS. 1 and 2. The stapler 10 of my invention is similar to existing end to end anastomotic staplers, commonly called "EEA staplers". The stapler 10 includes an actuating head portion 12 attached to an elongated hollow, tubular body 14 with a handle 16 on the opposed end of the body 14 from the head 12. The body 14 may include a bend, as shown in FIG. 1, to better conform to the shape of the patient's bowel. The handle 16 includes a rotary control 18 for actuating an anvil 22 of the stapler 10 in a conventional fashion, as will be described. The handle 16 also includes a trigger 20 for firing of the staples in a generally conventional manner, as will be described. The handle 16 may further include a conventional safety lock (not shown in detail) which acts to prevent firing of the staples until the anvil 22 is in the appropriate position relative to the head 12.

The construction of the head 12 differs significantly from existing EEA staplers. Unlike existing EEA staplers, the anvil 22 and an associated stapling mechanism (shown generally at 34) are positioned perpendicular to the longitudinal axis 24 of the head 12, as shown in FIG. 1. This construction allows the stapler 10 to perform side to end and side to side anastomosis. The end 26 of the head 12 is rounded to minimize potential trauma to the bowel. In constructing the head 12, it is important to minimize the widest dimension of the head 12 about the longitudinal axis 24. This dimension, shown at 28 in FIG. 1, will generally be along the axis of the anvil 22. The widest dimension 28 should be generally equal to the diameter of a circular head of conventional EEA staplers, which is generally about 30–35 mm. The widest dimension 28 is, therefore, less than about 35 mm for a conventional stapler 10 for application in the bowel. This dimension needs to be selected to allow the bowel, or other hollow viscus, to accept the head 12 of the stapler 10 without damage. The stapler 10 may be made of any size, as with conventional staplers, with the dimension 28 essentially the size of the stapler 10. Typical sizes would be 21, 25, 28 and 33 mm.

In addition to the dimensional considerations, the head 12 of my invention will require right angle drives for both the stapling mechanism 34 and operation of the anvil 22. The staples used in the head 12 are conventional staples positioned opposed from the anvil 22 in the conventional manner and are, therefore, not shown in detail. Additionally, the staples may further be fired together with an internal ring-shaped knife for trimming of the excess bowel portions, as conventional in the art. The staples and trimming knife of the stapling mechanism 34 do not form an essential part of the inventive concept of my invention and are, therefore, not shown in detail. FIG. 1 does schematically illustrate one type of right angle actuator for stapling mechanism 34 for firing of the staples (and for actuation of the trimming knife, if present). The right angle actuator includes a rod 30 extending along the inside of the tube 14 and movable along the tube by trigger 20 through a conventional linkage (not shown). The rod 30 includes a ramp 32 at the end thereof which will engage and actuate the stapling mechanism 34 which is shown schematically in FIG. 1. It will be apparent that many other right angle actuators are possible, with the present system being only a representative example.

The anvil 22 also requires a right angle drive. In operation, the anvil 22 can move relative to the head 12 by actuation of control 18. An open position of the anvil 22 relative to the head 12 is shown in phantom in FIG. 1. The operation of the anvil 22 is substantially the same as existing EEA staplers, except for the inclusion of a right angle drive. A stem 36 of anvil 22 will threadingly engage a rotatable sleeve (not shown) which is rotated by controller 18 through a rotatable shaft (not shown) extending through the tubular body 14. A pair of bevel gears may be provided within the head 12 between the rotatable sleeve and the rotatable shaft to accomplish the right angle drive. Bevel gears are well known for providing a right angle rotational drive. Other right angle rotational drives may be utilized, such as a flexible rotary shaft.

A circular stapler 10 for side to end and side to side anastomosis according to my invention operates as follows. The stapler 10 is inserted into the lower bowel segment to be attached. At the anastomosis site, the anvil 22 is advanced to the open position (shown in phantom in FIG. 1). The anastomosis sites of the two bowel segments to be attached are positioned between the anvil 22 and the head 12, and the anvil 22 is tightened by operation of the control 18 to clamp the relevant sections of the two bowel segments together. Known pull strings, and the like, may be used to assure the proper positioning of the bowel segments to be attached around stem 36. The trigger 20 is actuated to fire staples and the trimming knife, if any.

The anastomosis is now complete and the stapler 10 may be removed with any trimmed portions and pull string, or the like, secured between the anvil 22 and the head 12. The above operation is identical to existing EEA staplers except that the present invention allows for the side of the lower bowel segment to be attached to the end or to the side of the other bowel segment to be attached. Existing EEA staplers do not provide for this type of attachment between bowel segments.

Figure 3:
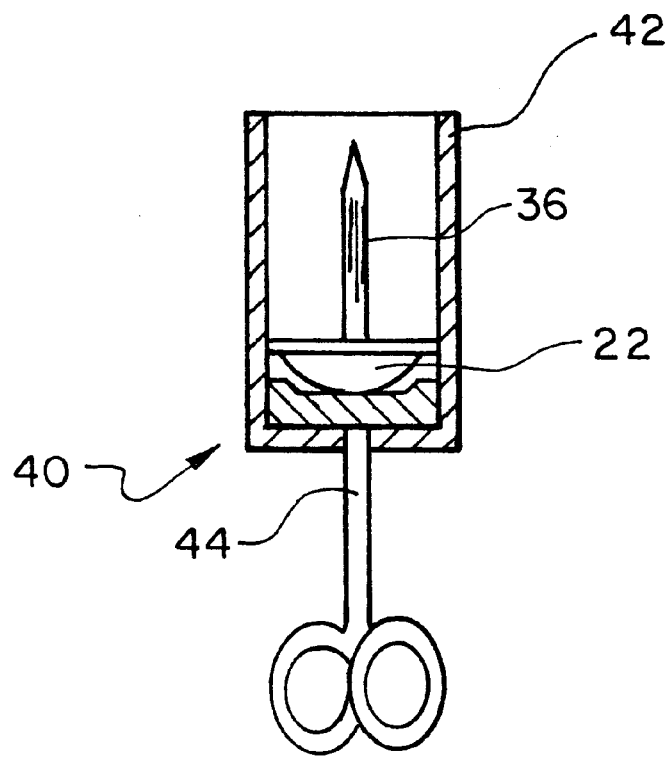
FIG. 3 is a side view of an anvil applicator for use with the stapler shown in FIG. 1.

The present stapler 10 will be particularly advantageous for performing the second stage of a two-stage Hartman operation. In the first stage of a two-stage Hartman operation, the patient undergoes a temporary colostomy with the upper portion of the colon extending to the dermis of the patient to which a colostomy bag is attached, with the lower portion of the colon being closed for subsequent reattachment in the second stage. In the second stage, the present invention allows for easy reattachment by inserting the stapler 10 into the upper bowel segment and attaching the side of the upper bowel segment to the (previously closed) end of the lower bowel segment. In such an operation, it would be advantageous to remove the anvil 22 from the stapler 10 and advance the anvil 22 transanally through the lower bowel portion to the anastomosis site. The stem 36 of the anvil 22 can be removed from the associated elements of the stapler 10 with a conventional bayonet fitting, as known in the art. In order to further assist the attachment of the anvil 22 with the head 12 of the stapler 10 at the anastomosis site, the present invention contemplates the use of an anvil applicator 40 to receive and advance the anvil 22, as shown in FIG. 3. The anvil applicator 40 is simply constructed and is formed of an anvil receiving sleeve 42 with a reciprocating, movable plunger 44 therein upon which the anvil 22 is mounted. The anvil applicator 40 greatly simplifies the operation where the anvil 22 is attached to the head 12 at the anastomosis site, such as in the second stage of a two-stage Hartman operation where the anvil applicator 40 with anvil 22 can be advanced transanally to the anastomosis site. When in position, at the anastomosis site, the plunger 44 can be advanced to move the anvil 22 and the stem 36 into engagement with the head 12 of the stapler 10. The removal of the anvil 22 from the head 12 is similar to the removable anvil provided in conventional staplers. As known in the art, when the anvil of a stapler is attached to the stapler at the anastomosis site, it is common for the stem of the anvil to be pushed through a bowel portion to be attached, such as the closed lower end of a bowel segment in the second stage of a two-stage Hartman operation. In such a procedure, there is no need for pull strings to secure the relevant portions of the bowel around the stem of the anvil, as will be evident to those of ordinary skill in the art.

The anvil applicator 40 of the present invention is not limited for use with anvils 22 of the stapler 10 of the present invention. The anvil applicator 40 may also be used with conventional anvils where the anvil is to be attached to a conventional stapler at the anastomosis site. The anvil applicator 40 greatly simplifies the attachment of any anvil to the corresponding stapler.

Figure 4:
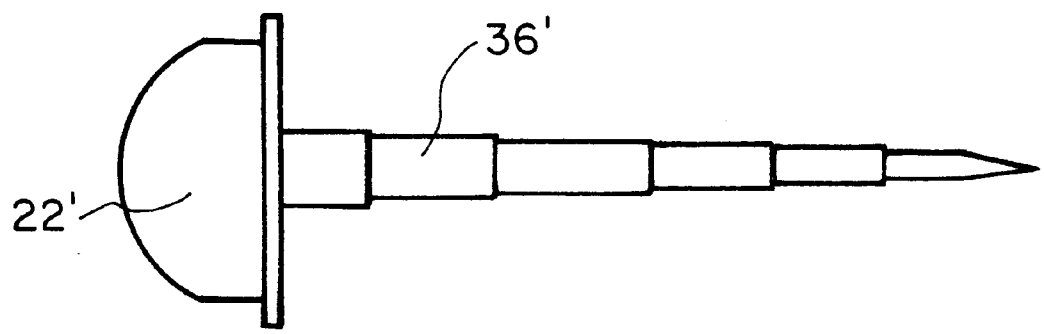
FIG. 4 is a side view of a modified anvil for use with the stapler shown in FIG. 1.

FIG. 4 illustrates a modified anvil 22' according to the present invention. In certain open procedures, the position of the bowel within the operating environment can make it difficult to attach the stem 36 of the anvil 22 to the head 12 in operations where the anvil 22 is attached to the stapler 10 at the anastomosis site. In order to simplify this problem, a modified anvil 22 is provided with a telescoping extendable stem 36'. The extendable stem 36' may be on the order of 12 inches and is intended to give more room for easier attachment of the anvil 22' to the stapler 10. Once the stem 36' and the corresponding element of the head 12 have been attached, the rotary controls of the stapler 10 can be used to properly advance the anvil 22' towards the head 12 in a conventional fashion. The extension of the stem 36' allows the surgeon to make this attachment in a more convenient and easily accessible location. The modified anvil 22' is not limited for use with the stapler 10 of the present invention. It is also believed to solve problems with conventional end to end staplers. Specifically, the same problems arise with end to end staplers in certain open surgical procedures. If the anvil 22' is used exclusively with end to end staplers, the telescoping stem 36' may be replaced with an extended, flexible stem member, since in a conventional end to end anastomosis stapler, the extendable stem 36' can be allowed to run the entire length of the handle portion thereof. The flexibility in such a stem would accommodate the bend normally found in the extended handle of an end to end anastomosis stapler. Additionally, the stems 36 and 36' of anvils 22 and 22', respectively, should also be made as small as possible in diameter to minimize the trauma when these elements are pushed through associated tissue.

My invention is not intended to be limited to bowel operations, but could be used for anastomosis of any hollow viscus. According to my invention, the anvil 22 and the associated stapling mechanism 34 are positioned perpendicular to the axis 24 of the head 12. It will be apparent that various modifications may be made to the present invention without departing from the spirit and scope thereof. Therefore, the scope of the present invention is intended to be defined by the appended claims and equivalents thereto.

I claim:

1. An anastomotic surgical stapler comprising:

an actuating head portion, said head portion including:

i) a detachable anvil with a stem engagable with a remainder of said head portion, said anvil receiving and closing the staples of a closed loop of staples, and ii) an associated stapling mechanism within said head portion for firing said closed loop of staples against said anvil when said anvil and stem are attached to said remainder of said head portion, wherein said anvil, said stem and said stapling mechanism are positioned perpendicular to a longitudinal axis of said head portion;

an elongated tubular body attached to and extending from said head portion, wherein said anvil, said stem and said stapling mechanism are perpendicular to a longitudinal axis of said tubular body at the position where said tubular body is attached to said head portion; and a handle on an opposed end of said tubular body from said head portion, wherein said stapler may selectively be used for both side to side and end to side anastomosis.

2. The stapler of claim 1 wherein said handle includes a rotary control for actuating said anvil and a trigger for firing staples in said stapling mechanism.

3. The stapler of claim 1 wherein an end of the head portion is rounded to minimize potential trauma to the patient.

4. The stapler of claim 3 wherein said head portion further includes a recess spaced from said rounded end, said recess receiving said anvil.

5. The stapler of claim 1 wherein a widest dimension of said head portion about said longitudinal axis is less than 35 mm.

6. The stapler of claim 1 further including an anvil applicator adapted to selectively receive said anvil.

7. The stapler of claim 6 wherein said anvil applicator includes an anvil receiving sleeve and a reciprocating movable plunger mounted within said anvil receiving sleeve.

8. The stapler of claim 1 wherein said anvil includes a telescoping stem.

9. An anastomotic surgical stapler for selectively performing both side to side and side to end anastomosis, said stapler comprising:

a rigid, tubular body, a handle at on end of said body, and an actuating head portion at an opposite end of said body, said head portion including i) a stapling mechanism for firing a closed loop of staples substantially radially of the head portion to attach the side of a first hollow viscus surrounding said stapling mechanism to a second hollow viscus, and ii) a separate, detachable anvil having a stem on said anvil for coupling said anvil to said stapling mechanism, wherein said anvil receives said closed loop of staples to attach a side or an end of the second hollow viscus surrounding said anvil to the side of the first hollow viscus.

10. The stapler of claim 9 wherein in at least one position said stem is on the order of about 12" long.

11. The stapler of claim 9 wherein said stem includes telescoping segments.

12. The stapler of claim 11 wherein said anvil and said stapling mechanism are orientated perpendicular to a longitudinal axis of said head portion.

13. The stapler of claim 9 wherein said anvil and said stapling mechanism are orientated perpendicular to a longitudinal axis of said head portion.

* * * * *